United States Patent
Deane et al.

(10) Patent No.: US 10,603,060 B2
(45) Date of Patent: Mar. 31, 2020

(54) ATTACHMENT ASSEMBLIES FOR ORAL HYGIENE DEVICES HAVING IMPROVED FLUID CHAMBER, FLUID CHANNEL, FLUID EXIT HOLE, AIR INLET HOLE, AND AIR CHANNEL FEATURES

(71) Applicant: KONINKLIJKE PHILIPS N.V., Eindhoven (NL)

(72) Inventors: Steven Charles Deane, Cambridge (GB); Johannes Hendrikus Maria Spruit, Waalre (NL); Adrianus Wilhelmus Dionisius Maria Van Den Bijgaart, Helvoirt (NL); Valentina Lavezzo, Heeze (NL); Lucas Scheffers, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/061,394

(22) PCT Filed: Dec. 5, 2016

(86) PCT No.: PCT/IB2016/057345
§ 371 (c)(1),
(2) Date: Jun. 12, 2018

(87) PCT Pub. No.: WO2017/103725
PCT Pub. Date: Jun. 22, 2017

(65) Prior Publication Data
US 2019/0038302 A1  Feb. 7, 2019

Related U.S. Application Data

(60) Provisional application No. 62/267,594, filed on Dec. 15, 2015.

(51) Int. Cl.
*A47L 13/22* (2006.01)
*A61B 17/24* (2006.01)
(Continued)

(52) U.S. Cl.
CPC ........ *A61B 17/244* (2013.01); *A46B 11/0006* (2013.01); *A46B 11/0013* (2013.01);
(Continued)

(58) Field of Classification Search
CPC .............. A61B 17/244; A46B 15/0081; A46B 15/0051; A46B 11/0006; A46B 11/0013; A46B 11/0062; A46B 11/06
See application file for complete search history.

(56) References Cited

U.S. PATENT DOCUMENTS 4,672,953 A   6/1987  DiVito
5,779,654 A   7/1998  Foley et al.
(Continued)

FOREIGN PATENT DOCUMENTS

DE  202015000686 U1  7/2015
WO  2015140247 A1   9/2015
WO  2016051287 A1   4/2016

OTHER PUBLICATIONS

Epstein et al: "Bacterial Biofilm Shows Persistent Resistance to Liquid Wetting and Gas Penetration"; PNAS, Jan. 18, 2011. vol. 108, No. 3, pp. 995-1000.
(Continued)

*Primary Examiner* — Jennifer C Chiang

(57) ABSTRACT

Attachment assemblies for oral hygiene devices and, in particular, attachment assemblies having improved designs to more effectively clean an individual's tongue or other inter-oral surface are described herein. These improved attachment assembly correspond, amongst other aspects, to improved fluid chamber configurations, improved fluid
(Continued)

channel configurations, improved fluid exit hole configurations, improved air inlet hole configuration, and air channel features. Furthermore, these improvements to attachment assemblies are capable of being implemented separately from, or in combination with, one another.

15 Claims, 6 Drawing Sheets

(51) Int. Cl.
A46B 11/00 (2006.01)
A46B 15/00 (2006.01)
A46B 11/06 (2006.01)

(52) U.S. Cl.
CPC .......... *A46B 11/0062* (2013.01); *A46B 11/06* (2013.01); *A46B 15/0051* (2013.01); *A46B 15/0081* (2013.01)

(56) References Cited

U.S. PATENT DOCUMENTS

| 6,139,558 | A | * | 10/2000 | Wagner | A61B 17/244 132/322 |
| 6,739,782 | B1 | | 5/2004 | Rehkemper et al. | |
| 8,801,316 | B1 | | 8/2014 | Abedini | |
| 9,265,513 | B2 | * | 2/2016 | Ripich | A61B 17/244 |
| 10,188,414 | B2 | * | 1/2019 | Ripich | A61B 17/244 |
| 2003/0083680 | A1 | * | 5/2003 | Jousson | A61B 17/244 606/161 |
| 2010/0223742 | A1 | | 9/2010 | Kang | |
| 2017/0333063 | A1 | * | 11/2017 | Jivan | A61B 17/244 |

OTHER PUBLICATIONS

Gomez-Pereira et al: "Development and Testing of a Tongue Brush to Deliver Long Lasting Fresh Breath"; Philips Research Technical Note, Nov. 2015, 37 Page Document.

Hartley et al: "Tongue Microbiota and Malodour"; Microbial Ecology in Health and Disease, 1999, vol. 11, pp. 226-233.

Hartley et al: "The Tongue Microbiota of Low Odour and Malodorous Individuals"; Microbial Ecology Inhealth and Disease; vol. 9, 1996, pp. 215-223.

Roldan et al: "A Combined Therapeutic Approach to Manage Oral Halitosis: A 3 Month Prospective Case Series"; J Periodontol, Jun. 2005, pp. 1025-1033.

Slot et al: "Treatment of Oral Malodour.Medium-Term Efficacy of Mechanical and/or Chemical Agents: A Systematic Review"; J Clin Periiodontol, vol. 42(Suppl 16), pp. S303-S316, 2015.

* cited by examiner

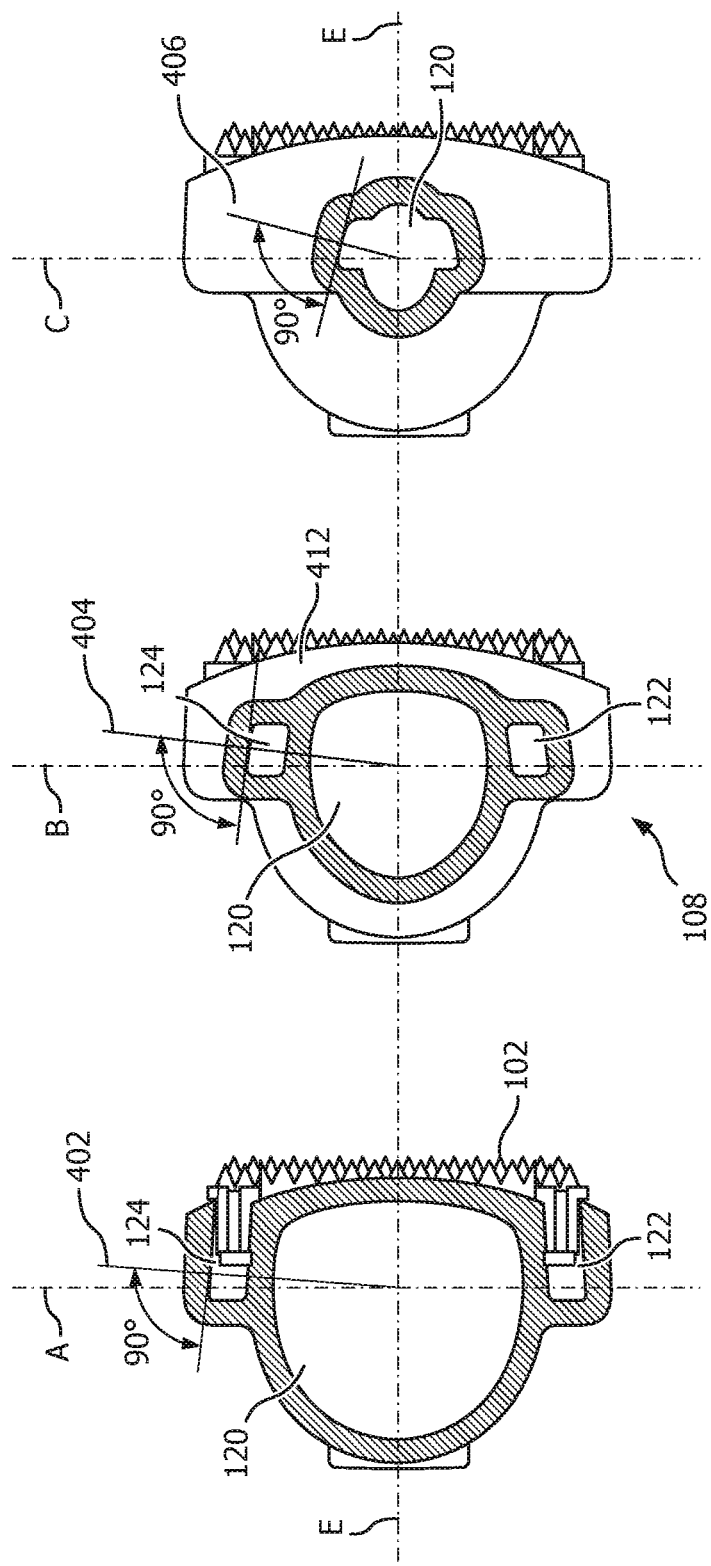

ATTACHMENT ASSEMBLIES FOR ORAL HYGIENE DEVICES HAVING IMPROVED FLUID CHAMBER, FLUID CHANNEL, FLUID EXIT HOLE, AIR INLET HOLE, AND AIR CHANNEL FEATURES

CROSS-REFERENCE TO PRIOR APPLICATIONS

This application is the U.S. National Phase application under 35 U.S.C. § 371 of International Application No. PCT/IB2016/057345, filed on Dec. 5, 2016, which claims the benefit of U.S. Provisional Patent Application No. 62/267,594, filed on Dec. 15, 2015. These applications are hereby incorporated by reference herein.

BACKGROUND OF THE INVENTION

1. Field of the Invention

The present disclosure generally relates to attachment assemblies for oral hygiene devices and, in particular, attachment assemblies having improved designs to more effectively clean an individual's tongue or other inter-oral surface. In particular, the present disclosure generally relates to improved designs to fluid chambers, fluid channels, fluid exit holes, air inlet holes, and air channels for such attachment assemblies.

2. Description of the Related Art

The presence of odorous volatile organic compounds, otherwise known as oral malodor or bad breath, is an all too common problem for individuals in today's modern society. At some point in time, most individuals have experienced, or been in close proximity to individuals suffering from, oral malodor. Having unpleasant mouth odor is a tremendous hindrance to an individual's daily life—it effects one's confidence level, one's ability to communicate with others, and one's ability to establish meaningful relationships with others. Such oral malodor, however, can be rooted in larger underlying issues, such as bacteria inhabiting one's tongue. This bacteria possesses enzymes that generate volatile sulphur compounds, which generate the unpleasant smells and effects associated with oral malodor.

Removal of such bacteria is one main goal for eliminating oral malodor. Biofilm layers present on the tongue, and in particular between papillae on the tongue, is the common home for such bacteria. However, removing these thick biofilms is a difficult task by conventional techniques, such as tongue scrapers and mouthwashes. These techniques further do not provide an individual with long-lasting fresh, and pleasant, breath.

There are generally two types of treatment options for oral malodor: (i) chemical, and (ii) mechanical. Conventional chemical treatments typically corresponds to techniques that kill bacteria on the tongue biofilm and/or neutralize odor thereon. Such chemical treatments are effective, however they commonly last just a few hours as the chemicals are not able to penetrate the biofilms deeply where a majority of the bacteria that causes oral malodor live. Conventional mechanical treatments typically corresponds to techniques that attempt remove the bacteria that causes oral malodor from the tongue. Such conventional mechanical treatments typically provide only a minimal amount of odor protection (e.g., 30 minutes), as they are not effective at removing bacteria growing between papillae on the tongue.

One effective option is to combine both the chemical and mechanical treatment techniques in order to better mitigate oral malodor. While there some devices that provide both chemical and mechanical treatment of oral malodor, these devices have significant remaining issues. One way to provide this combined treatment is via a brush that mechanically can clean the tongue, while a pump coupled to the brush pumps fluid to the tongue to provide the chemical portion of the treatment. However, a handle portion of the oral hygiene device that includes a fluid reservoir and a pump therein can be large. Furthermore, the pump itself can malfunction, thereby rendering the combined treatment process ineffective.

In one embodiment, these devices are known as "pump free" devices, which provide chemical treatment without the use of a pump to eject fluid, such as a mouthwash, to a user's tongue. These pump free devices harness rotational forces to force fluids out of a brush head, onto a contact pad, which interacts and cleans the individual's tongue. However, creating a brush head that effectively transports fluid to the contact pad, while also minimizing the load on the oral hygiene device driving the brush head, can be difficult. Furthermore, configuring the brush head such that it minimizes leakage, reenter of contaminants from the tongue (e.g., the biofilm on the tongue), and effectively provides fluid at various angles of use, is not easy. Thus, it would be beneficial if there were improved designs for brush heads for treating oral malodor such that these devices function and operate in a more effective manner. One way to overcome this potential issue is to include a pump-free attachment assembly, or brush head, that utilizes centrifugal forces to "pump" fluid out of the attachment assembly. This improved functionality further allows for many existing electronic oral healthcare devices to still be used while employing the pump-free attachment assembly.

SUMMARY OF THE INVENTION

Accordingly, it is an objective of this disclosure to provide an attachment assembly for an oral hygiene device that is capable of effectively reducing interpapillary bacteria, thereby improving an individual's breath. This objective is achieved according to the present disclosure by providing various improvements to attachment assemblies that combat oral malodor. In particular, such improvements relate to improved fluid chamber, fluid channel, fluid exit hole, air inlet hole, and air channel design.

In a first exemplary embodiment, an attachment assembly for an oral hygiene device is described. The attachment assembly includes a connection member, a main attachment, and a contact pad. The connection member has a first end and a second end, where the first end of the connection member is configured to couple to a handle portion of the oral hygiene device. The main attachment is coupled to the connection member at the second end and includes a fluid a chamber. The fluid chamber is substantially elongated along a longitudinal axis of the oral hygiene device, substantially enclosed within the main attachment, operable to have a fluid for use with the oral hygiene device stored therein, and substantially circular in cross section along the longitudinal axis such that a moment of inertia of the oral hygiene device remains substantially constant regardless of an amount of fluid stored within the fluid chamber. The contact pad is operable to receive fluid from the fluid chamber to clean a surface during operation of the oral hygiene device.

In a second exemplary embodiment, an attachment assembly for use with an oral hygiene device configured to deliver fluid to a contact pad without use of a pump is described. The attachment assembly includes a fluid chamber for storing fluid to be delivered to the contact pad during operation of the oral hygiene device. The attachment assembly also includes one or more fluid channels that extend along a first portion of one or more side walls of the attachment assembly. A first end of the one or more fluid channels is in fluid communication with the fluid chamber at a first end of the attachment assembly. A second end of the one or more fluid channels is in fluid communication with a first fluid exit hole. Furthermore, the first fluid exit hole fluidly connects the one or more fluid channels and the contact pad.

In a third exemplary embodiment, an attachment assembly for use with an oral hygiene device that minimizes leakage due to air entering the attachment assembly is described. The attachment assembly includes a substantially elongated main attachment including a fluid chamber therein for storing fluid. The attachment assembly also includes one or more fluid exit holes in fluid communication with the fluid chamber. The one or more fluid exit holes are located at a first position along a longitudinal axis of the substantially elongated main attachment, and along a first side of the substantially elongated main attachment. The attachment assembly further includes one or more air inlet holes in fluid communication with the fluid chamber. The one or more air inlet holes are located at a second position along the longitudinal axis of the substantially elongated main attachment, and along a second side of the substantially elongated main attachment, where the first side and the second side are substantially opposite from one another.

In a fourth exemplary embodiment, an attachment assembly for an oral hygiene device that minimizes reentry of contaminants therein is described. The attachment assembly includes a main attachment, a contact pad, and one or more fluid exit holes. The main attachment has a fluid chamber located therein. The contact pad is located on a first side of the main attachment. The one or more fluid exit holes are located on the contact pad. The one or more fluid exit holes are also in fluid communication with fluid stored within the fluid chamber, and have a substantially narrow diameter such that the attachment assembly is configured to regulate outflow of the fluid stored within the fluid chamber during operation of the oral hygiene device.

In a fifth exemplary embodiment, another attachment assembly that minimizes reentry of contaminants therein is described. The attachment assembly includes a main attachment, a contact pad, and one or more fluid exit holes. The main attachment has a fluid chamber located therein. The contact pad is located on a first side of the main attachment. The one or more fluid exit holes are located on an outer edge of the contact pad. The one or more fluid exit holes are substantially tube shaped such that they extend from the first aside of the main attachment towards a surface to be cleaned. The main attachment is configured to oscillate in a first direction and a second direction by a first distance. Furthermore, a length of the substantially tube shaped one or more fluid exit holes is at least twice as large as the first distance.

In a sixth exemplary embodiment, yet another attachment assembly for an oral hygiene device that minimizes reentry of contaminants therein is described. The attachment assembly includes a main attachment, a contact pad, a first fluid exit hole, and a second fluid exit hole. The main attachment has a fluid chamber located therein. The contact pad is located on a first side of the main attachment. The first fluid exit hole is located along a first edge of the contact pad along a first side of the main attachment. The second fluid exit hole is located along a second edge of the contact pad along a second side of the main attachment.

In a seventh exemplary embodiment, still another attachment assembly that minimizes reentry of contaminants therein is described. The attachment assembly includes a fluid chamber, one or more channels, and one or more additional channels. The fluid chamber is substantially elongated along a longitudinal axis of the oral hygiene device. The one or more channels have a first end and a second end. The one or more channels are located on a first side of, and are in fluid communication at the first end with a lower end of, the fluid chamber. The one or more additional channels are located on the first side of the fluid chamber. The one or more additional channels are in fluid communication with the one or more channels at the second end, and are in fluid communication with the fluid chamber at an upper end of the main fluid chamber.

BRIEF DESCRIPTION OF THE DRAWINGS

The above and other features of the present invention, its nature and various advantages will be more apparent upon consideration of the following detailed description, taken in conjunction with the accompanying drawings in which:

FIGS. 4A, 4B and 4C are an illustrative diagrams of cross-sectional views taken along lines A-A, B-B, and C-C of FIG. 1B of attachment assembly 100, respectively, in accordance with various embodiments;

DETAILED DESCRIPTION OF EXEMPLARY EMBODIMENTS

Figures 1A, 1B:
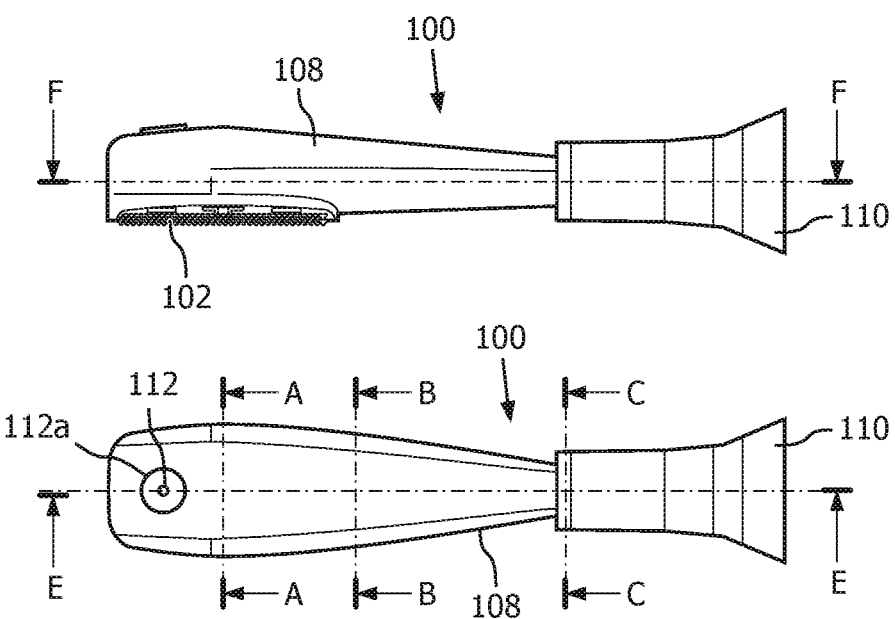
FIGS. 1A and 1B are perspective views of an attachment assembly 100 in accordance with various embodiments.

The present invention may take form in various components and arrangements of components, and in various techniques, methods, or procedures and arrangements of steps. The referenced drawings are only for the purpose of illustrated embodiments, and are not to be construed as limiting the present invention. Various inventive features are described below that can each be used independently of one another or in combination with other features. Furthermore, as used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. As employed herein, the statement that two or more parts or components "engage" on another shall mean that the parts exert a force against one another either directly or through one or more intermediate parts or components. As employed herein, the term "number" shall mean one or an integer greater than one (e.g., a plurality).

As used herein, a "substantially fluid tight seal" means that two surfaces sealingly engage each other in a manner that substantially limits passage of fluid or gas between the two surfaces (e.g., no more than 5% passage). Furthermore, as used herein, the term "fluid communication" or "fluidly communicating" means that two or more parts are engaged such that fluid or gas may pass between the two or more parts in a manner that substantially limits leakage of fluid or gas between the two or more parts (e.g., no more than 5% leakage).

As used herein, the term "sealingly" or "sealed" in the context of an engagement, attachment or coupling means that two parts are coupled to one another with a substantially fluid tight seal.

Direction phrases used herein including, but not limited to, top, bottom, right, left, upper, lower, front, back, rear, and derivatives thereof, relate to the orientation of the elements shown in the drawings and are not limiting upon the claims unless expressly recited therein.

FIGS. 1A, 1B, 2A and 2B are perspective views of attachment assembly 100 in accordance with various embodiments. Attachment assembly 100, in the illustrative, non-limiting embodiment, is a brush head having a substantially circular fluid chamber located therein. Attachment assembly 100, for example, may correspond to a brush head coupled to an electric oral hygiene device to assist in cleaning an individual's tongue. For example, attachment assembly 100 may be used to minimize the effects of oral malodor.

Figure 2A:
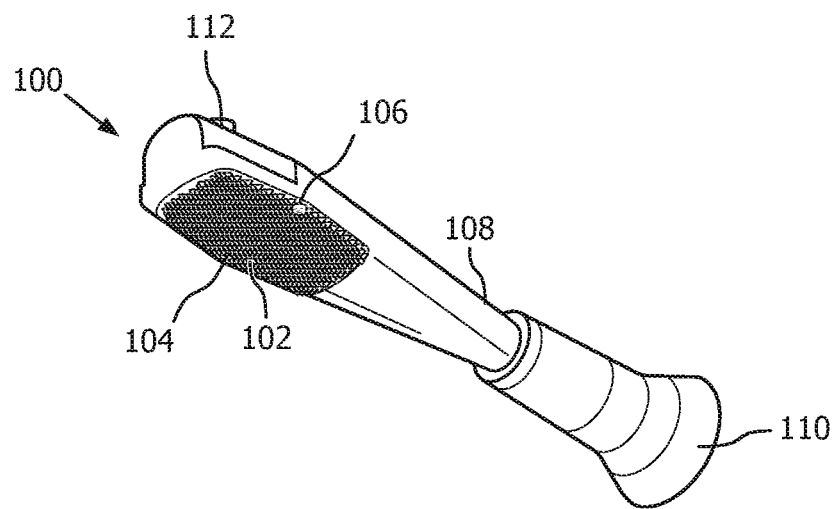
FIGS. 2A and 2B are illustrative diagrams of an attachment assembly 100 in accordance with various embodiments.

As seen in FIG. 2A, attachment assembly 100 includes, in an exemplary embodiment, a connection member 110. Connection member 110 enables attachment assembly 100 to connect to an oral hygiene device at a proximal end thereof. Distal end of connection member 110 connects to a main attachment 108 of attachment assembly 100 at a proximal end of the main attachment 108. Main attachment 108 of attachment assembly 100, in the illustrative embodiment, is approximately cylindrical, or an elongated cylindrical shape, along a longitudinal axis E-E shown in FIG. 1B extending through attachment assembly 100 and the oral hygiene device coupled thereto. The distal end of main attachment 108 of attachment assembly 100 is the portion that typically enters an individual's mouth.

Figure 2B:
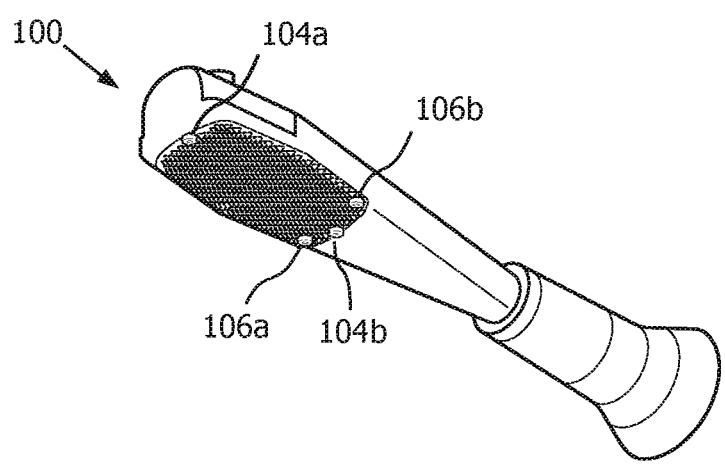

Located along a first side of main attachment 108 of attachment assembly 100 proximate the distal end, in the exemplary embodiment, is contact pad 102, which is shown in FIGS. 1A, 2A, and 2B, and described in greater detail below. Contact pad 102 may include multiple instances of a bristle (e.g., bristles), which serve to interact with an individual's tongue. In one particular example, the various bristles of contact pad 102 may interact with the various papillae on an individual's tongue which, in combination with a fluid (e.g., mouthwash), may aid in cleaning and removing biofilm from the tongue. In one embodiment, one or more fluid exit holes 104, 106 as shown in FIG. 2A (and described in greater detail below) may also be located along a portion of contact pad 102, such as along an edge of contact pad 102. The general placement of fluid exit holes 104, 106, therefore, is typically approximately centered along edges on either side of contact pad 102, such as shown in FIG. 2A. This general positioning of fluid exit holes 104, 106 maintains suitable moment of inertia parameters for attachment assembly 100. However, it can be appreciated that the fluid exit holes could be located in other positions, depending on the geometry of a particular attachment assembly 100, and the mode of operation of the device to which it is attached. For example, fluid exit holes could be positioned in the upper or lower portions of contact pad 102, either centered, such as fluid exit holes 104a, 104b in FIG. 2B, or on either side of the contact pad 102, such as fluid exit holes 106a, 106b of FIG. 2B.

In another embodiment, one or more air inlet holes 112, as shown in FIG. 1B (and described in greater detail below), may be located on a second side of attachment assembly 100 proximate the distal end, where the second side is an opposite side of main attachment 108 from the first side that includes contact pad 102.

As can be seen in FIGS. 1A and 1B, main attachment 108 of attachment assembly 100 is generally cylindrical in shape. At the proximal end, main attachment 108 may taper slightly such that a cross sectional diameter of main attachment 108 at the proximal end (e.g., along line C-C) is smaller than a cross sectional diameter midway along a length of main attachment 108 (e.g., along line B-B). Furthermore, main attachment 108 may taper slightly such that a cross sectional diameter of main attachment 108 at the distal end is smaller than a cross sectional diameter midway (e.g., along line B-B) along the length of main attachment 108. Persons of ordinary skill in the art will recognize that the shape of main attachment 108, and attachment assembly 100 in general, as described above is merely exemplary, and any other suitable configuration may be used so long as attachment assembly 100 is operable to fit within a user's mouth and minimizes any adverse physical effects, such as gagging.

FIG. 1A further illustrates the exemplary configuration of attachment assembly 100. In the illustrated embodiment, a longitudinal axis F-F runs through a substantially central portion of connection member 110 and main attachment 108 of attachment assembly 100. In the embodiment shown in FIG. 1A, axis F-F is slightly closer to the first side of attachment assembly 100, that containing contact pad 102, as opposed to second side of attachment assembly 100, such that axis F-F is located slightly off a central axis, however persons of ordinary skill in the art will recognize that this is merely exemplary. Furthermore, the dual tapered configuration of main attachment 108 of attachment assembly 100 is further displayed in FIG. 1B. For example, along a mid-point of contact pad 102 (e.g., along line A-A), main attachment 108 may be larger in cross section than at proximal or distal ends of main attachment 108. As mentioned in greater detail below, this may occur to assist in transporting fluid from a fluid chamber 120 located within attachment assembly 100 to contact pad 102 for assisting in cleaning an individual's tongue.

FIG. 1B illustrates attachment assembly 100 as viewed looking down from the opposite side of contact pad 102. Running along a central axis of attachment assembly 100 is axis E-E, which is substantially equidistant from an edge on either side of main attachment 108 along its length. In one embodiment, the proximal end of main attachment 108 is "thinner" such that a distance along axis C-C from either edge of main attachment 108 to axis E-E is less than a distance along axis A-A or B-B from either edge of main attachment 108 to axis E-E.

Figure 3A:
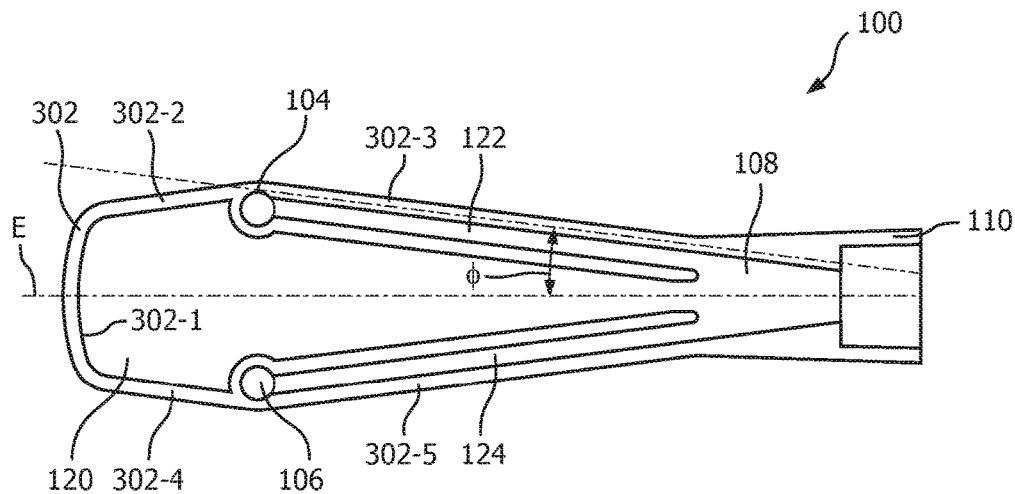
FIGS. 3A and 3B are illustrative diagrams of a cross-sectional view taken along line F-F of FIG. 1A of attachment assembly 100 in accordance with various embodiments.

FIG. 3A is an illustrative diagram of a cross-sectional view taken along line F-F of attachment assembly 100 as shown in FIG. 1A, in accordance with an embodiment. Main attachment 108 of attachment assembly 100, as seen in FIG. 3A, includes outer wall 302, which is generally annular in shape, however it may include one or more non-circular portions. Wall 302 is substantially thin, of the order of a few millimeters (or less), and is symmetric about a longitudinal axis E. Wall 302 forms a cavity within attachment assembly 100 which serves as fluid chamber 120 for retaining fluid therein. In the illustrative, non-limiting embodiment of FIG. 3A, wall 302 includes two upper side portions, 302-2, 302-4, that are located on opposite sides of longitudinal axis E. Each of the two upper side portions 302-2, 302-4 connect to a substantially perpendicular portion 302-1 of wall 302 at an upper end (e.g., distal end thereof. In one exemplary embodiment, upper side portions 302-2, 302-4 may be slightly angled with respect to longitudinal axis E and may connect on one side to perpendicular portion 302-1 of wall 302, and connect to at the opposite end to lower side portion 302-3, 302-5, respectively, which may also be angled with respect to longitudinal axis E, and may be at a different angle than upper side portions 302-2, 302-4. Main attachment 108 connects to connection member 110 at a proximal end thereof. Fluid exit holes 104, 106, are typically located in the area where upper side portions 302-2, 302-4 and lower side portions 302-3, 302-5 intersect.

In the exemplary embodiment, upper side portions 302-2 and 302-4 have a substantially same angle and radius. In other words, a length of each of upper side portions 302-2 and 302-4 is equal and a distance from longitudinal axis E of both upper side portions 302-2 and 302-4 with respect to longitudinal axis E is also equal. Furthermore, upper side portions 302-2 and 302-4 connect to lower side portions 302-3 and 302-5, respectively, such that a substantially constant side portion is formed on either side of longitudinal axis E. Similarly, lower side portions 303-3 and 303-5 have a substantially same angle and radius such that a length of each of lower side portions 303-3 and 302-5 is equal and a distance from longitudinal axis E of both lower side portions 302-3 and 302-5 with respect to longitudinal axis E is also equal.

In the illustrative embodiment, fluid chamber 120 includes one or more channels 122 and 124, which are configured to run along a length of lower side portions 302-3 and 302-5, respectively, of wall 302 along the cross-sectional plane. Channels 122 and 124, in one embodiment, have a substantially same angle with respect to longitudinal axis E as lower side portions 302-3 and 302-5 of wall 302. In the embodiment shown in FIG. 3A, each of channels 122 and 124 are substantially straight and have a substantially constant angle Φ with respect to longitudinal axis E along a length of fluid chamber 120. In one exemplary embodiment, angle Φ is approximately 7-degrees, however persons of ordinary skill in the art will recognize that this is merely exemplary. Channels 122 and 124 are in fluid communication with a portion of fluid chamber 120 at proximal end of main attachment 108 of attachment assembly 100. Fluid within fluid chamber 120 is, therefore, capable of being communicated into channels 122 and 124 when the oral hygiene device that attachment assembly 100 is coupled to is being operated.

Located at the points where upper side portions 302-2, 302-4 and lower side portions 302-3, 302-5 of wall 302 meet, are, in one embodiment, fluid exit holes 104 and 106, respectively. Fluid exit holes 104, 106 are substantially circular in shape, and are located at an end of channels 122 and 124. As described in more detail below, when in operation, fluid enters fluid channels 122 and 124 from lower (proximal) portion of fluid chamber 120, which is located at an opposite end of channels 122 and 124 where fluid exit holes 104, 106 are located. In one embodiment, fluid is operable to exit fluid exit holes 104, 106 when the fluid receives a sufficient force to move the fluid from lower portion of fluid chamber 120 to fluid exit holes 104, 106. Thus, fluid channels 122 and 124 are, in the exemplary embodiment, in fluid communication with fluid exit holes 104, 106, respectively.

Figure 3B:
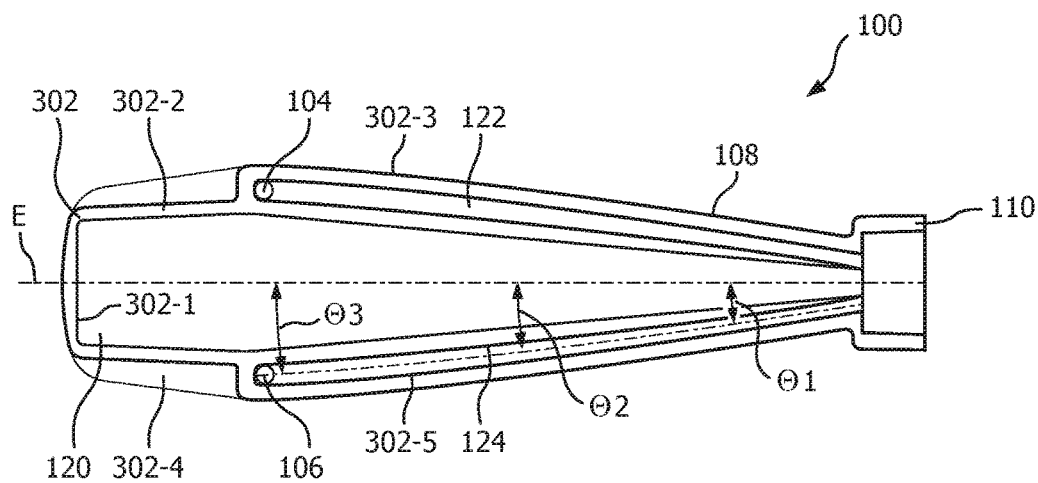

FIG. 3B is illustrative diagram a cross-section view taken along line F-F of attachment assembly 100 in accordance with another embodiment. This embodiment is substantially similar to the embodiment shown in FIG. 3A, with the exception that the embodiment shown in FIG. 3B includes channels 122 and 124 each have a substantially varying angle with respect to longitudinal axis E. Channels 122 and 124 of the exemplary embodiment have a varying angle along longitudinal axis E such that the angle of channels 122 and 124 proximate lower (proximal) end differs from the angle of channels 122 and 124 proximate fluid exit holes 104, 106.

In one non-limiting embodiment, channels 122 and 124 each have a first angle $\Theta 1$ proximate lower (proximal) end, a second angle $\Theta 2$ at a midpoint between fluid exit holes 104, 106, and the proximal end of the fluid chamber 120, and a third angle $\Theta 3$ at a point near fluid exit holes 104, 106, where each of first angle $\Theta 1$, second angle $\Theta 2$, and third angle $\Theta 3$ are with respect to longitudinal axis E. For example, first angle $\Theta 1$ may be approximately 10-degrees, second angle $\Theta 2$ may be approximately 7-degrees, and third angle $\Theta 3$ may be approximately 4-degrees with respect to longitudinal axis E. In one embodiment, channels 122 and 124 have an average angle along their length, with respect to longitudinal axis E, of approximately 7-degrees (e.g., the average of first angle $\Theta 1$, second angle $\Theta 2$, and third angle $\Theta 3$ is approximately 7-degrees).

In a typical operation, attachment assembly 100 rotates about longitudinal axis E with a peak to peak amplitude of approximately 10-degrees at a frequency of approximately 200-300 Hz. By including fluid channels 122 and 124, attachment assembly 100, when tilted, does not experience troubles delivering fluid through exit holes 104, 106 due fluid located at the proximal portion of the fluid chamber 120 (i.e. near the connection member 110) not experiencing the centrifugal forces necessary to eject fluid out of fluid exit holes 104, 106. The acceleration of the fluid in a tangential direction is lower than if the fluid behaved as a rigid body in fluid chamber 120. Channels 122 and 124 thus enable the fluid to exit fluid chamber 120 through fluid exit holes 104, 106 with greater ease and in fuller volume. Channels 122 and 124, in the exemplary embodiments, transmit the fluid more effectively due to their fluid column design and the increased effects of centrifugal force on the fluid therein, which is proportional to the distance from longitudinal axis E, as well as an angle of channels 122 and 124, and the angular velocity of fluid located therein. The fluid transport, in general, is driven by the centrifugal force on the wall of channels 122 and 124, thereby causing the direction of motion of the fluid therein to be towards fluid exit holes 104, 106, respectively. The centrifugal forces proximate the proximal end of fluid chamber 120 are limited due to the smaller radius with respect to longitudinal axis E. Therefore, by increasing the angle at the proximal end thereof, such as in the embodiment shown in FIG. 3B, the amount of centrifugal force driving the fluid towards exit holes 104, 106 increases. As the centrifugal forces are larger proximate exit holes 104, 106, the angle of fluid channels 122 and 124 is capable of being lessened such that a balanced pumping effect is present over a total length of fluid channels 122 and 124.

While both a constant angle, as in FIG. 3A, and a varying angle, as in FIG. 3B, for channels 122 and 124 are described above, a steeper angle at the proximal end of channels 122 and 124 increase the centrifugal forces felt by fluid at at the proximal end of channels 122 and 124. This is further highlighted by the smaller angle (e.g., third angle Θ3), which is closer to fluid exit holes 104, 106, which enables the fluid to flow out of fluid exit holes 104, 106 even if channels 122 and 124 are only partially full of fluid.

The width of channels 122 and 124, in one exemplary embodiment, is sufficiently small such that turbulent and vortex motion of fluid therein is minimized. By minimizing these types of motion for the fluid, maximum use of centrifugal forces to drive fluid from fluid chamber 120 through fluid channels 122 and 124 and then out of fluid exit holes 104, 106 is created. In one exemplary embodiment, fluid channels 122 and 124 have a width of approximately 2 millimeters or less, however persons of ordinary skill in the art will recognize that this is merely exemplary.

The theoretical moment of inertia for an attachment assembly 100 having a substantially circular fluid chamber is approximately 110 mm$^2$ for an empty fluid chamber 120, and approximately 135 mm$^2$ a full fluid chamber 120. In practice, the actual moment of inertia of attachment assembly 100 having a circular fluid chamber remains substantially constant regardless of whether fluid chamber 120 is empty half-full, or full. The theoretical moment of inertia of an attachment assembly 100 having substantially rectangular fluid chamber is approximately 110 g·mm$^2$ for an empty fluid chamber, and approximately 150 g·mm$^2$ for a full fluid chamber. Thus, the moment of inertia of the attachment assembly having a substantially rectangular fluid chamber increases substantially depending on the fluid level within the fluid chamber.

Persons of ordinary skill in the art will recognize that although the aforementioned embodiments describe a fluid chamber that is substantially circular, the foregoing descriptions may be applicable to both a substantially circular fluid chamber as well as a rectangular or non-circular fluid chamber. Furthermore, in one embodiment, a substantially circular fluid chamber, such as fluid chamber 120, may be used within an attachment assembly that, itself (e.g., main attachment 108), is not necessarily circular. Persons of ordinary skill in the art will recognize that different geometries may be used in the design of attachment assembly, and the illustrated embodiments described herein are merely exemplary.

For a pump-free design, for example, fluid chamber 120 of attachment assembly 100 should hold between 1-8 mL of fluid, such as a mouthwash, which is to be dispensed during use. In one particular embodiment, fluid chamber 120 is capable of storing between 2-4 mL of fluid therein. The mouthwash serves to assist in removing biofilm from between papillae of the tongue, as well as increasing biofilm eradication, when used in combination with the bristles on contact pad 102 (e.g., chemical and mechanical treatment). The fluid, however, when oscillating about attachment assembly 100, contributes to the moment of inertia of attachment assembly 100. Typically, oral hygiene devices, such as those operable to receive attachment assembly 100, expect to receive an attachment assembly having a substantially constant moment of inertia. This is because oral hygiene devices are designed to work with a limited range of moment of inertias for attachment assemblies. By the addition of a fluid to attachment assembly 100, this affects the moment of inertia of attachment assembly 100, and therefore, the functionality of the oral hygiene device could be, potentially, greatly impacted.

When in use, the fluid that is actively being communicated from fluid chamber 120 within attachment assembly 100 to fluid exit holes 104, 106 in contact pad 102 is needed to move, and therefore, "feel," or be affected by, centrifugal forces. By using fluid channels, such as fluid channels 122, 124 of attachment assembly 100, fluid residing within fluid channels 122, 124 experiences the largest amount of centrifugal force while fluid within fluid chamber 120 experiences the smallest amount of centrifugal force.

At various points along axis E-E in FIG. 1B are exemplary cross-sectional cutaway points on axis F-F, labeled via lines A-A, B-B, and C-C, which are described in more detail below with reference to FIGS. 4A, 4B and 4C, respectively. In particular, the various cross-sectional views in FIGS. 4 A-C show fluid chamber 120 operable to store fluid, such as mouthwash, therein. The cross-sectional views also show fluid channels 122 and 124. In one exemplary embodiment, the cross-sectional view along line A-A shows a substantially circular configuration of fluid chamber 120. Fluid chamber 120, as viewed along cross-sectional lines B-B and C-C is still substantially circular, albeit the diameter of substantially circular fluid chamber 120 is smaller at lines B-B and C-C than at line A-A, as main attachment 108 of attachment assembly 100 may be tapered in design along axes F-F and E-E.

To minimize the effects of the centrifugal forces, by configuring fluid chamber 120 to be substantially circular along a length of attachment assembly 100, a substantially thin layer of fluid (e.g., approximately less than 0.2 millimeters in thickness), when stored within fluid chamber 120, will move at the driving frequency of the oral hygiene device when in operation. Therefore, configuration of fluid chamber 120 such that it is substantially circular enables the contribution of fluid from fluid chamber 120 to the moment of inertia to be less than 50% as compared to a non-circular (e.g., rectangular) fluid chamber. Furthermore, fluid chamber 120, as seen within FIGS. 4A-4C, is substantially tapered in structure such that, at line A-A, the cross section of fluid chamber 120 is substantially larger than the cross section of fluid chamber 120 at line B-B, which further is substantially larger than the cross section of fluid chamber 120 at line C-C. Persons of ordinary skill in the art will recognize, however, that fluid chamber 120 need not be perfectly circular at any point along the length of main attachment 108 of attachment assembly 100, and the aforementioned is merely exemplary.

A further benefit of the substantially circular design of fluid chamber 120 of attachment assembly 100 is a decrease in foam being generated within fluid chamber 120. Foam typically is created within fluid chamber 120 due to sloshing of fluid therein, which generally occurs due fluid within fluid chamber 120 moving. The creation of foam inhibits refilling of fluid chamber 120 by a user. This is additionally beneficial in that the effective volume of fluid released by attachment assembly 100 when in use increases by reducing the amount of foam within fluid chamber 120.

As seen in each cross-sectional view of FIGS. 4A-4C, an exterior wall of fluid channels 122 and 124 of attachment assembly 100, in one non-limiting, exemplary embodiment, is substantially perpendicular to a radial line extending outward from the intersection of longitudinal axis E. For example, the exterior wall of fluid channels 122 and 124 may be bisected by radial line 402, as seen in FIG. 4A. Radial line 402, in the illustrative embodiment, extends from the intersection of cross-sectional line A-A and line E-E. Similarly, radial lines 404 and 406 shown in FIGS. 4B and 4C, respectively, each may also bisect the exterior wall of fluid channel 124 (or fluid channel 122) along cross-sectional lines B-B and C-C, respectively. By having radial lines 402, 404, and 406 bisecting the exterior wall of channels 122 and 124, the exterior wall will continually be tangential to the axis of rotation of attachment assembly 100 along the length of channels 122 and 124. By doing this, any component of the generated centrifugal force that would lead to internal agitation of fluid within channels 122 and 124 (e.g., swirling of the fluid), is minimized.

Furthermore, as shown in FIGS. 4A-4C, each of fluid channels 122 and 124 is configured, in the exemplary embodiment, such that the exterior wall of fluid channels 122 and 124 maintain a perpendicular relationship to radial line 402, 404, and 406, for example, along the length of fluid channels 122 and 124. Still further, the substantially circular cross-sectional nature of fluid chamber 120 along longitudinal axis E is maintained, thereby minimizing the effects of fluid within fluid chamber 120 on the moment of inertia of attachment assembly 100.

There is a relationship between the amount of fluid delivered by, and an angle of, attachment assembly 100. For previously designed attachment assemblies that do not include fluid channels 122 and 124, the percentage of fluid delivered steadily decreases as the angle of attachment assembly 100 increases with respect to gravity. This means that, as a user increases the angle of application of attachment assembly 100 coupled to their oral hygiene device, the amount of fluid that is provided decreases. For example, as the angle of operation goes, for the attachment assembly without channels, from being substantially horizontal (e.g., 0-degrees with respect to gravity) to substantially vertical (e.g., 90-degrees with respect to gravity), the amount of fluid delivered as a percentage of volume decreases from over 90% to approximately 60%.

Addition of fluid channels 122 and 124 enables attachment assembly 100 to provide a more consistent output of fluid, regardless of the angle of operation. For example, when attachment assembly 100 is operated at a substantially horizontal angle with respect to gravity, the output flow of fluid from attachment assembly 100 is substantially equal to the output flow of fluid when attachment assembly 100 is operated substantially at a substantially vertical angle with respect to gravity (e.g., 90-degrees). This enables an individual to more freely use their oral hygiene device including attachment assembly 100, without being required to maintain a substantially horizontal orientation of their device, and still obtaining a consistent flow of fluid from attachment assembly 100.

Figure 5:
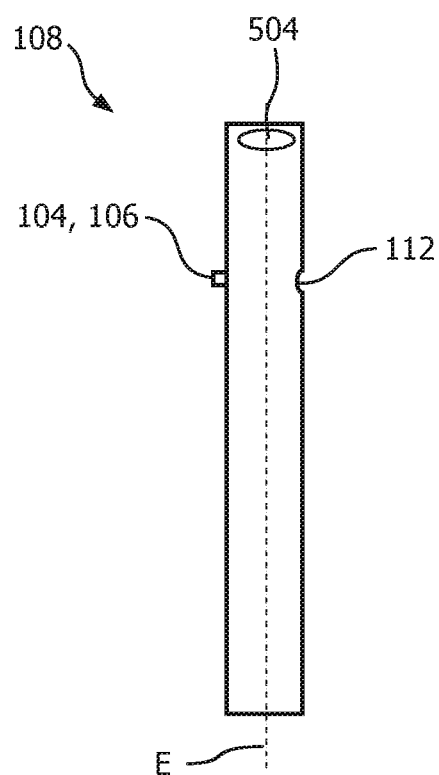
FIG. 5 is an illustrative diagram of air inlet hole positioning for attachment assembly 100 in accordance with various embodiments.

FIG. 5 is an illustrative diagram of air inlet hole 112 positioning for attachment assembly 100 in accordance with various embodiments. Air leakage may occur with attachment assembly 100 due to pressure differences between air inlet holes 112, and fluid exit holes, 104, 106. If there is an acceleration experienced by air bubbles, or air, trapped within fluid chamber 120, for instance due to gravity or other motion, under pressure caused by air entering through an air inlet hole from the external environment, this may cause fluid to be pushed out of fluid exit holes 104, 106.

In the illustrative, non-limiting embodiment of FIG. 5, main attachment 108 includes an air inlet hole 112, approximately equidistant from the edges of main attachment 108 (as seen in FIG. 1B and at a substantially same position along longitudinal axis E as fluid exit holes 104, 106. In the exemplary embodiment, air inlet hole 112 is located on an opposite side of attachment assembly 100 as fluid exit holes 104 and 106. For example, if fluid exit holes 104 and 106 are located on a first side (e.g., a same side as contact pad 102), air inlet hole 112 would be located on an opposite side of main attachment 108. By placing air inlet hole 112 at a substantially similar location along longitudinal axis E, as fluid exit holes 104 and 106. By doing this, an air bubble 504, for example, when attachment assembly 100 is vertically oriented, is not in communication with air inlet hole 112, and therefore new air bubbles are not introduced into fluid chamber 120.

In another exemplary embodiment, not shown, instead of a single air inlet hole 112 being used, multiple air inlet holes 112 may be implemented. In this particular scenario, the various instances of air inlet holes 112 are each placed substantially proximate to one another. Furthermore, the multiple instances of air inlet hole 112 may then be placed at a substantially same height as one another such that they are all within the general plane, or height, of fluid exit holes 104 and 106.

A size of fluid exit holes 104, 106 is configured such that each fluid exit hole is substantially large enough that a fluidic resistance of fluid exiting fluid exit holes 104, 106 is minimized. In one exemplary embodiment, the size of fluid exit holes 104, 106 is less than 0.7 millimeters, such as 0.5 millimeters or 0.6 millimeters. In another illustrative embodiment, the size of fluid exit holes 104, 106 is between approximately 0.5 millimeters and approximately 0.6 millimeters. However, persons of ordinary skill in the art will recognize that the precise value of fluid exit holes 104, 106 is merely exemplary, and any diameter of fluid exit holes 104, 106 that is less than 0.7 millimeters may exhibit suitable flow rate behaviors. The flow rate of fluid exit holes 104, 106 having a diameter greater than, or equal to, 0.7 millimeters is such that when attachment assembly 100 is at an angle of approximately 30-degrees with respect to gravity, flow rate starts substantially high (e.g., 10 mL/minute) after about 10 seconds of use. However, the flow rate falls off exponentially such that, after about 30 seconds, the flow rate is substantially low (e.g., less than 1 mL/minute). In this scenario, a user will experience a severe lack of fluid on contact pad 102 after a very short amount of time, thereby significantly hindering the cleaning process.

When fluid exit holes 104, 106 are configured to have a diameter, D, of approximately 0.5 millimeters, the flow rate remains substantially constant over the first 30 seconds of operation. For example, between times 0 and 30 seconds of operation, the flow rate of fluid out of exit holes 104, 106 remains between approximately 2 mL/min and 4 mL/min. By decreasing the size (e.g., the diameter) of fluid exit holes 104, 106 to approximately between 0.5-0.6 mm, or less than 0.7 millimeters, the fluid flow rate from fluid exit holes 104, 106 is maintained substantially constant over the initial 30 second brushing interval, or cleaning session.

Figure 6:
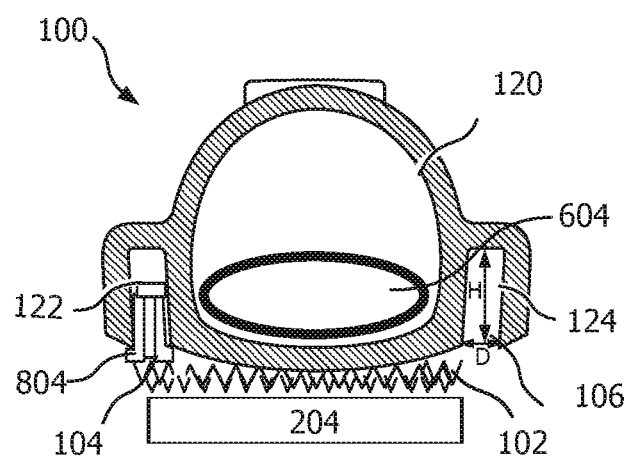
FIG. 6 is an illustrative diagram of a fluid exit hole for attachment assembly 100 in accordance with various embodiments.

FIG. 6 is a cross-sectional view of an upper portion of attachment assembly 100 including contact pad 102 and, in particular, fluid exit holes 104, 106. As previously mentioned, attachment assembly include fluid chamber 120, which stores a fluid 604 therein. Furthermore, at various positions along an edge or side of contact pad 102, are one or more fluid exit holes 104, 106. During operation, attachment assembly 100 moves approximately 1 millimeter peak to peak, resulting in an approximately 1 millimeter long slug of fluid exiting fluid exit holes 104, 106 in the process. When the attachment assembly moves downward toward the surface of the tongue 616, some of the fluid may reenter fluid exit holes 104, 106. The exact amount of fluid that will re-enter fluid exit holes 104, 106 is not static, but dependent on various factors including, but not limited to, surface tension on exit holes 104, 106, wetting, and viscosity. The amount of fluid, conversely, that exits fluid exit holes 104, 106 is dependent on other factors, including, but not limited to, exit hole diameter, D, the number of exit holes, and the driving force from the oral hygiene device, which determines an outflow rate of fluid from fluid exit holes 104, 106. The outflow rate due to each stroke of attachment assembly 100 is proportional to the square of the diameter of the fluid exit hole (e.g., $D^2$), while the outflow rate due to the driving force increases with fluidic resistance, which is proportional to a length of fluid exit holes 104, 106 14 and the diameter of the fluid exit hole to the fourth power (e.g., $D^4$). If fluid re-enters fluid exit holes 104, 106, it may contain some biofilm from the individual's tongue 204, which can mix with the sterile fluid (e.g., mouthwash) located in fluid chamber 120. This can compromise the fluid stored within fluid chamber 120, as well as cause contaminant buildup along fluid exit holes 104, 106, degrading the functionality and performance of attachment assembly 100 over time.

Fluid channels 122, 124, in one exemplary embodiment, are substantially tube shaped in structure in the illustrative embodiment. This results in, for example, fluid exit hole 106 at the exit of fluid channel 124 having an inner diameter substantially smaller than 1 millimeter, such as 0.5-0.6 millimeters in diameter. Furthermore, the height, H, of the fluid exit holes is approximately 2.5 millimeters. By being approximately 2.5 millimeters in height, the distance that biofilm on tongue 204 needs to travel back through fluid exit holes 104, 106, up the height of the fluid channels at the fluid exit holes, and then into the length of the fluid channels 122, 124 in order to reenter fluid chamber 120 is greatly increased. In the exemplary embodiment, height H of fluid channel 124 is more than the length of typical motion of attachment assembly 100 in operation, which great reduces the amount of biofilm and mouthwash mixture that can re-enter the fluid chamber 120. This is particularly useful when fluid chamber 120, and fluid channels 122 and 124, are nearly empty, as fluid channels 122 and 124 may, in this particular scenario, become partially filled with air, resulting in a partial amount of internal mixing that transports contaminants into fluid chamber 120 from fluid channels 122 and 124.

When attachment assemblies are tilted at a significant angle with respect to gravity, fluid may not adequately be provided to contact pad 102 from fluid chamber 120. This problem is addressed in greater detail by implementing fluid channels, such as fluid channels 122 and 124, into attachment assembly, such as shown in FIG. 6. However, fluid may still be present in channels 122 and 124 when the oral hygiene device including attachment assembly 100 is no longer being operated. As described previously, the contamination from biofilm on an individual's tongue can be pulled back into fluid chamber 120 through fluid exit holes 104, 106 and channels 122 and 124, respectively. Furthermore, fluid channels 122 and 124 may, themselves, trap air, which can inhibit a user's ability fill fluid chamber 120. Still further, proper fluid delivery may not occur for individuals operating their oral hygiene such that the handle of the oral hygiene device is higher than the distal end of attachment assembly 100.

In normal use, the fluid chamber (120) is filled with fluid (604), such as mouthwash. When the oral hygiene device is stored when not in use, it is typically positioned vertically or horizontally, with the attachment assembly 100 attached. Leakage of fluid from the fluid chamber out the exit holes may occur even when the oral hygiene device is not in use, if there is a pressure difference between the air inlet hole and the fluid exit holes. To reduce fluid leakage from the fluid exit holes (104, 106) when the oral hygiene device is not in operation (i.e. stored), the material of the fluid exit holes can be made sufficiently hydrophobic such that fluid in the fluid chamber is prevented from exiting the fluid exit holes. The capillary forces of the exit holes are governed by the Young-Laplace equation:

$$\Delta p = \frac{2\gamma \cos\theta}{a} \quad (1)$$

Where $\Delta p$ is the pressure drop across the interface, $\gamma$ is the surface tension, $\theta$ is the contact angle between the fluid and wall material, and $\alpha$ is the radius of the tube. This can also be expressed as the height that fluid would rise (or fall for contact angles >90 degrees) in an open tube at equilibrium.

$$h = \frac{2\gamma \cos\theta}{\rho g a} \quad (2)$$

Where h is the height of the liquid, $\rho$ is the density of the liquid, and g is the acceleration due to gravity.

For typical mouthwashes, $\gamma=0.032$ J/m2, and density is near that of water. Thus, we can calculate that for a 0.5 mm diameter exit hole, if completely hydrophobic ($\theta=180$ degrees), a fluid height of ~26 mm would be needed to overcome the meniscus pressure and force fluid to enter the exit hole. For a less extreme contact angle, $\theta=120$ degrees still gives a fluid height of ~13 mm to overcome the resistance to enter the exit holes. This is sufficient to prevent leakage due to normal handling accelerations. An additional advantage of such hydrophobic exit holes is that if the device is stored in air and allowed to dry, it prevents a risk of mouthwash drying and leaving residues in the exit holes, which could block them.

However, mouthwashes typically contain surfactants and various other compounds, so that in general it is hard to achieve contact angles >60 degrees a much lower contact angle than would be seen with water on the same surfaces. In this case, the leakage prevention still occurs, but is due to a slightly different implication of the same effect. Now the relevant meniscus is formed at the end of the exit hole, where the surface turns though 90 degrees, and the fluid must form a convex meniscus to exit the exit hole.

A similar force, which for contact angles <90 degrees has the sense of resisting fluid outflow occurs, and is given by the equation:

$$h = \frac{2\gamma \sin\theta}{\rho g a} \quad (3)$$

Using the same parameters as before, for a contact angle of 30 degrees, this gives a pressure to release fluid equivalent to a fluid height of ~13 mm, and for 60 degree contact angles this increases to 22.6 mm. This force becomes negative for contact angles >90 degrees, indicating that if the fluid meniscus reaches this point (i.e. it overcomes the forces given earlier preventing the fluid entering the exit hole), then it will experience a force tending to cause outflow, to enable the fluid surface to reduce its radius of curvature.

Thus, even for contact angles <90 degrees, a fluid retaining force remains, and is increased by making the exit hole material more hydrophobic, particularly on the exposed surface near the exit. While these forces are sufficient to significantly prevent leakage of fluid, they do not prevent fluid outflow in operation, as the acceleration forces at the exit hole in operation are ~190 g, which is large compared to the resistance due to the hydrophobic forces.

For example, as seen in FIG. 6, a liner of hydrophobic material 804 is inserted into the fluid channel 122, which limits fluid egress from fluid exit hole 104. When the oral hygiene device is in operation and the attachment assembly 100 is moving about an axis, the motion of the attachment assembly will generate fluid pressure sufficient to overcome the hydrophobic retention material such that fluid can exit the fluid exit hole.

A further step in preventing leakage can come from making the air inlet hole 112 from a hydrophobic material as well, or inserting a liner of hydrophobic material 112a in the air inlet hole that can also reduce the diameter of the air inlet hole, such as can be seen in FIG. 1B. There are additional advantages in making the air hole material more hydrophobic, but if the contact angle is <90 degrees, not too small (not the same size as or smaller than the fluid exit holes). Not only can this help to prevent leakage though the air inlet hole, in exactly the same way as for the fluid exit holes, but also it can help to allow easy air entry in use. In this case, the air inlet hole is not located at a location of strong acceleration in the direction of the hole, so during motion, motion forces do not help air come in. For hydrophilic materials, a meniscus pressure needs to be overcome to allow air to enter, which is calculated by the equations given. For small air inlet holes (which help prevent fluid leakage) this can be large enough to balance the fluid outflow forces at the exit holes, and cause flow to stop, which is undesirable. This determines the minimum air inlet hole size desirable. When the air inlet hole and its surrounding material is hydrophobic, then there is little barrier to air inflow, and not only is leakage prevented, but normal fluid outflow in operation is ensured.

Figure 7:
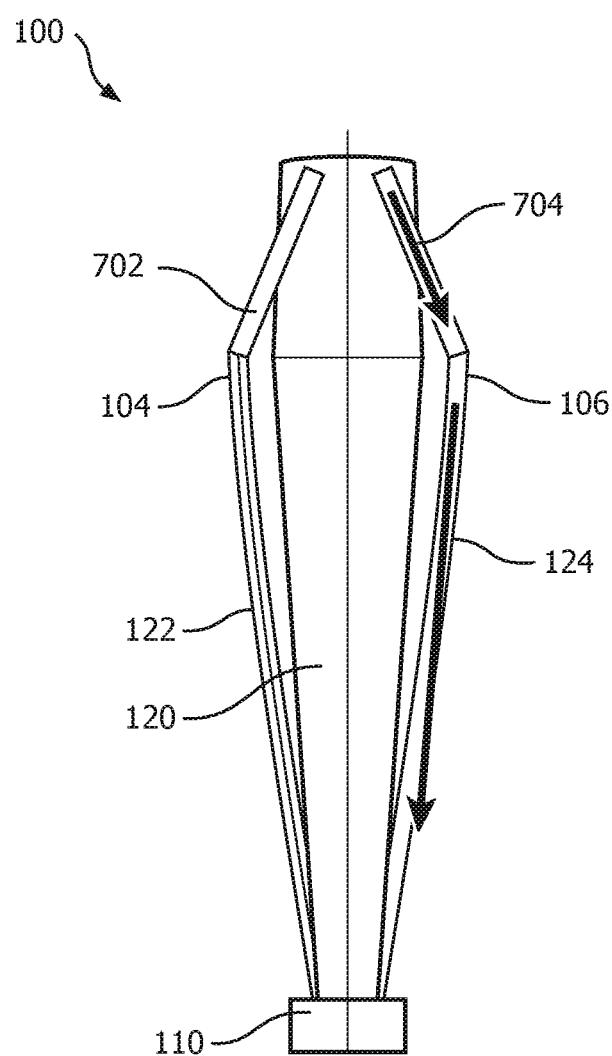
FIG. 7 is an illustrative diagram of attachment assembly 100 including air channels 10002, 1004 in accordance with various embodiments.

FIG. 7 is an illustrative diagram of another attachment assembly 100 in accordance with another embodiment that also includes air channels 702 and 704. Each of air channels 702, 704 extend from fluid exit holes 104, 106, respectively, to a distal end of fluid chamber 120. By including air channels 702, 704 into attachment assembly 100, air bubbles have a path to follow to easily be removed from fluid channels 122 and 124 when attachment assembly 100 is being filled. Furthermore, air channels 702, 704 enable air from the distal portion of fluid chamber 120 to enter fluid channels 122 and 124 when the oral hygiene device including attachment assembly 100 stops being operated, which can cause fluid within fluid channels 122 and 124 to reenter fluid chamber 120 without exit holes 104, 106 pulling, or sucking, in biofilm or other contaminants.

In one embodiment, a radius of air channels 702, 704 from the main longitudinal axis of attachment assembly 100 at which air channels 702, 704 join fluid chamber 120 is equal to or smaller than a radius of fluid channels 122 and 124. This can reduce fluid circulating through attachment assembly 100, thereby generating foaming with attachment assembly 100, which hinders fluid outflow during operation. As seen in FIG. 7, air channels 702, 704 are connected at exit holes 104, 106, and to fluid channels 122 and 124, respectively. Thus, a radius of air channels 702, 704 at distal end of fluid chamber 120 where air channels 702, 704 join fluid chamber 120 is equal to, or less than, a radius of fluid channels 122 and 124 where they join fluid chamber 120 at the proximal end thereof, adjacent to connection member 110. In one embodiment, air channels 702, 704 are in substantially fluid communication with fluid channels 122 and 124 as well as, or in addition to, being in fluid communication with fluid exit holes 104, 106.

As described above, air channels 702, 704, in the exemplary embodiment, are in fluid communication with fluid channels 122 and 124 at one end proximate fluid exit holes 104, 106, respectively, and at an opposite end, are in fluid communication with fluid chamber 120. Furthermore, fluid channels 122 and 124 are in fluid communication with fluid chamber 120. Thus, air channel 702, in combination with fluid channel 122, and air channel 704, in combination with fluid channel 124, essentially becomes a two-ended structure connecting at either end with fluid chamber 120. When the oral hygiene device that attachment assembly 100 stops being operated, air from the distal end of fluid chamber 120 is capable of entering air channels 702, 704, thereby enabling fluid to flow down into fluid channels 122 and 124, minimizing any suction that would occur at exit holes 104, 106.

Furthermore, when a user attempts to fill attachment assembly 100 with fluid, air located within air channels 702, 704 and/or fluid channels 122 and 124 is able to move to the top of fluid chamber 120, thereby minimizing air being trapped by fluid exit holes 104, 106. As yet another benefit, attachment assembly 100 will have increased performance when angled (e.g., when attachment assembly 100 is lower than a handle of the oral hygiene device attached thereto). This enables a user to be able to tilt their head upwards to better reach different regions of their mouth. This feature is accomplished by air channels 702, 704, in one embodiment, functioning as fluid channels and fluid channels 122 and 124 functioning as air channels.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An attachment assembly for use with an oral hygiene device configured to deliver fluid without use of a motorized pump of the oral hygiene device, the attachment assembly comprising:
a connection member having a proximal end configured to couple to a distal end of the oral hygiene device; and
a substantially elongated main attachment coupled to the connection member at the distal end of the connection member, the main attachment comprising:
a fluid chamber therein for storing fluid for use with the oral hygiene device;
a contact pad at a distal end of the main attachment on a first side thereof;
at least one fluid exit hole on the first side of the main attachment in fluid communication with the fluid chamber operable to receive fluid from the fluid chamber and deliver it to the contact pad;
an air inlet hole in fluid communication with the fluid chamber located on a second side of the main attachment, opposite the side of the main attachment where the contact pad is located; and
wherein fluid in the fluid chamber exits the at least one fluid exit hole during operation of the oral hygiene device.

2. The attachment assembly of claim 1, further comprising:
at least a first fluid channel extending along at least a portion of a first side of the fluid chamber within the main attachment, a first end of the first fluid channel in fluid communication with the fluid chamber at a first end thereof and the at least one fluid exit hole at a second end thereof; and
a second fluid channel extending along at least a portion of a second side of the fluid chamber opposite the first side of the fluid chamber, such that the first fluid channel and the second fluid channel are located on opposites sides of the contact pad, a first end of the second fluid channel in fluid communication with the fluid chamber at a first end thereof and the second at least one fluid exit hole at a second end thereof.

3. The attachment assembly of claim 2, wherein each of the first fluid channel and the second fluid channel are configured such that they have a substantially constant angle ($\phi$) with respect to the longitudinal axis of the attachment assembly along the length of the fluid channels.

4. The attachment assembly of claim 2, wherein:
each of the first fluid channel and the second fluid channel are configured such that they have a substantially varying angle with respect to the longitudinal axis of the attachment assembly along the length of the attachment assembly, the first fluid channel and the second fluid channel having the first angle with respect to the longitudinal axis at a first portion of the fluid channels proximate the first end of the fluid channel, the second angle with respect to the longitudinal axis at a second portion of the fluid channels proximate the middle of the fluid channels, and the third angle with respect to the longitudinal axis at a third portion of the of the fluid channels proximate the fluid exit hole.

5. The attachment assembly of claim 2, wherein:
the at least one fluid channel is configured such that an amount of fluid dispensed to the contact pad from the first fluid exit hole is substantially constant independent of an angle of the attachment assembly with respect to gravity.

6. The attachment assembly of claim 2, wherein the fluid chamber and the at least one fluid channel are configured such that fluid stored in the fluid chamber is forced out of the first fluid exit hole due to centrifugal forces exerted on the fluid stored within the fluid chamber during operation of the oral hygiene device.

7. The attachment assembly of claim 1, wherein the position of the at least one fluid exit hole and the position of the at least one air inlet hole are arranged such that each of the at least one fluid exit hole and the at least one air inlet hole are located at a substantially same position approximately midway along the longitudinal axis of the main attachment.

8. The attachment assembly of claim 2 wherein:
the at least one fluid channel is substantially tube shaped such that it extends from a first side of the main attachment outwards at a height H towards the at least one fluid exit hole;
the main attachment is configured to move a first distance during operation of the oral hygiene device to deliver fluid from the fluid channel to the at least one fluid exit hole; and
the height (H) of the substantially tube shaped portion of at least one fluid channel is at least twice as large as the first distance moved by the main attachment to prevent re-entry of fluid that has exited the fluid exit hole.

9. The attachment assembly of claim 1, wherein the contact pad comprises:
a plurality of elongated structures that are configured to contact the surface.

10. The attachment assembly of claim 1 further comprising a liner of hydrophobic material inserted into the at least one fluid exit hole to reduce the diameter of the fluid exit hole so as to reduce fluid exiting the fluid exit hole when the oral hygiene device is not in operation.

11. The attachment assembly of claim 1 further comprising a liner of hydrophobic material inserted into the at air inlet hole so as to reduce fluid exiting the air inlet hole when the oral hygiene device is not in operation.

12. An attachment assembly for an oral hygiene device configured to deliver fluid to a user's mouth without use of a pump in the oral hygiene device, the attachment assembly comprising:
a connection member at a proximal end thereof configured to connection to a distal end of the oral hygiene device;
a substantially elongated main attachment coupled at the proximal end thereof to a distal end of the connection member, the main attachment having a fluid chamber that is substantially elongated along a longitudinal axis of the attachment assembly;
a contact pad at a distal end of the main attachment on a first side thereof;
an air inlet hole in fluid communication with the fluid chamber located on a second side of the main attachment, opposite the side of the main attachment where the contact pad is located;
at least one fluid exit hole on the contact pad on the first side of the main attachment and at least a second fluid exit hole on an opposite side of the contact pad from the first at least one fluid exit hole;
a first fluid channel located on a first side of the fluid chamber, having a first end in fluid connection with the fluid chamber operable to receive fluid from the fluid chamber and a second end in connection with the first fluid exit hole;

a second fluid channel located on a second side of the fluid chamber opposite the side of the fluid chamber from the first fluid channel, having a first end in fluid connection with the fluid chamber operable to receive fluid from the fluid chamber and a second end in connection with the second fluid exit hole;

at least one first air channel located on the first side of the fluid chamber, having a first end in fluid connection with a distal end of the fluid chamber and a second end in connection with the first fluid channel at first fluid exit hole operable to remove air bubbles from the first fluid channel to the distal end of the fluid chamber;

at least one second air channel located on the second side of the fluid chamber, having a first end in fluid connection with a distal end of the fluid chamber and a second end in connection with the second fluid channel at second fluid exit hole operable to remove air bubbles from the second fluid channel to the distal end of the fluid chamber; and wherein during operation of the oral hygiene device, fluid stored within the fluid chamber is expelled from the at least one fluid exit hole.

13. The attachment assembly of claim 12, wherein:

the least one first air channel and the at least one second air channel function as fluid channels; and the first fluid channel and the second fluid channel function as air channels.

14. The attachment assembly of claim 12, wherein:

the first and second fluid channels are angled such that, at the first end, the fluid channel is at a first distance away from the longitudinal axis of the attachment assembly and, at the second end, the fluid channel is at a second distance away from the longitudinal axis; and the first distance is less than the second distance.

15. The attachment assembly of claim 12, wherein:

the at least one channel is configured such that it makes a first angle with the longitudinal axis such that the first angle is one of:

substantially constant along a length of both the at least one channel; and substantially varying along the length of both the at least one channel.

\* \* \* \* \*